(12) United States Patent
Kargar et al.

(10) Patent No.: US 8,363,782 B2
(45) Date of Patent: Jan. 29, 2013

(54) SYSTEM FOR CIRCULATORY BLOOD FLOW TRAVEL TIME DETERMINATION

(75) Inventors: Soroosh Kargar, Lake in the Hills, IL (US); Weng Lei, Mount Prospect, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 294 days.

(21) Appl. No.: 12/970,995

(22) Filed: Dec. 17, 2010

(65) Prior Publication Data

US 2011/0249789 A1  Oct. 13, 2011

Related U.S. Application Data

(60) Provisional application No. 61/322,976, filed on Apr. 12, 2010.

(51) Int. Cl.
 *G01N 23/04* (2006.01)
 *H05G 1/64* (2006.01)
(52) U.S. Cl. .......................... 378/62; 378/98.5; 378/114
(58) Field of Classification Search ................ 378/4, 19, 378/62, 98.5, 114
 See application file for complete search history.

(56) References Cited

U.S. PATENT DOCUMENTS

| 6,505,064 | B1 | 1/2003 | Liu et al. | |
|---|---|---|---|---|
| 2007/0206724 | A1* | 9/2007 | Sakaguchi et al. | 378/62 |
| 2008/0056445 | A1* | 3/2008 | Spahn | 378/62 |
| 2009/0003521 | A1* | 1/2009 | Camus et al. | 378/62 |

* cited by examiner

*Primary Examiner* — Irakli Kiknadze
(74) *Attorney, Agent, or Firm* — Alexander J Burke (57) ABSTRACT

An X-ray imaging system automatically calculates blood flow travel time by using an X-ray image acquisition system to initiate acquisition of images at a second anatomical site synchronized with introduction of contrast agent into a patient vessel at a first anatomical site. A detector automatically compares images, acquired at the second anatomical site in response to the introduction of contrast agent, with images of the second anatomical site acquired in the absence of a contrast agent, to detect when contrast agent reaches the second anatomical site via blood flow in a circulatory system of the patient. A calculator automatically calculates a blood flow travel time duration between the first and second anatomical sites based on the time elapsed between time of the introduction of contrast agent and a time the contrast agent reaches the second anatomical site in response to the detection. An output processor automatically generates a message indicating the calculated blood flow travel time.

18 Claims, 6 Drawing Sheets

FIGURE 6

SYSTEM FOR CIRCULATORY BLOOD FLOW TRAVEL TIME DETERMINATION

This is a non-provisional application of provisional application Ser. No. 61/322,976 filed Apr. 12, 2010, by S. Kargar et al.

FIELD OF THE INVENTION

This invention concerns an X-ray imaging system for automatically calculating blood flow travel time in response to time elapsed between time of introduction of contrast agent into a patient and a time the contrast agent reaches an anatomical site to be imaged.

BACKGROUND OF THE INVENTION

It is desirable to know the travel time of blood from Pulmonary Arteries to the left atrium, for example, for delaying X-ray imaging start in an imaging procedure. The capability of delaying X-ray imaging facilitates accurate left atrium imaging (e.g. 3D imaging) of the left Atrium and capture of functional details. Known systems lack a flexible, user friendly capability of automatically calculating blood flow travel time between user selected anatomical sites. A system according to invention principles addresses this deficiency and related problems.

SUMMARY OF THE INVENTION

A system automatically calculates a time required for blood to travel from Pulmonary Arteries to a heart Left Atrium, for example. An X-ray imaging system automatically calculates blood flow travel time by using an X-ray image acquisition system to initiate acquisition of images at a second anatomical site synchronized with introduction of contrast agent into a patient vessel at a first anatomical site. A detector automatically compares images, acquired at the second anatomical site in response to the introduction of contrast agent, with images of the second anatomical site acquired in the absence of a contrast agent, to detect when contrast agent reaches the second anatomical site via blood flow in a circulatory system of the patient. A calculator automatically calculates a blood flow travel time duration between the first and second anatomical sites based on the time elapsed between time of the introduction of contrast agent and a time the contrast agent reaches the second anatomical site in response to the detection. An output processor automatically generates a message indicating the calculated blood flow travel time.

DETAILED DESCRIPTION OF THE INVENTION

A system automatically calculates time required for blood to travel from Pulmonary Arteries to a heart Left Atrium, for example. A system according to invention principles automatically calculates travel time of blood flow between user selected different anatomical sites including from Pulmonary Arteries to a left atrium. In imaging a heart left atrium, a catheter is advanced via the right atrium and placed in a pulmonary artery of the heart and contrast agent is injected into the pulmonary arteries. The contrast agent travels from the Pulmonary arteries via lungs and pulmonary veins to the left atrium.

Figure 1:
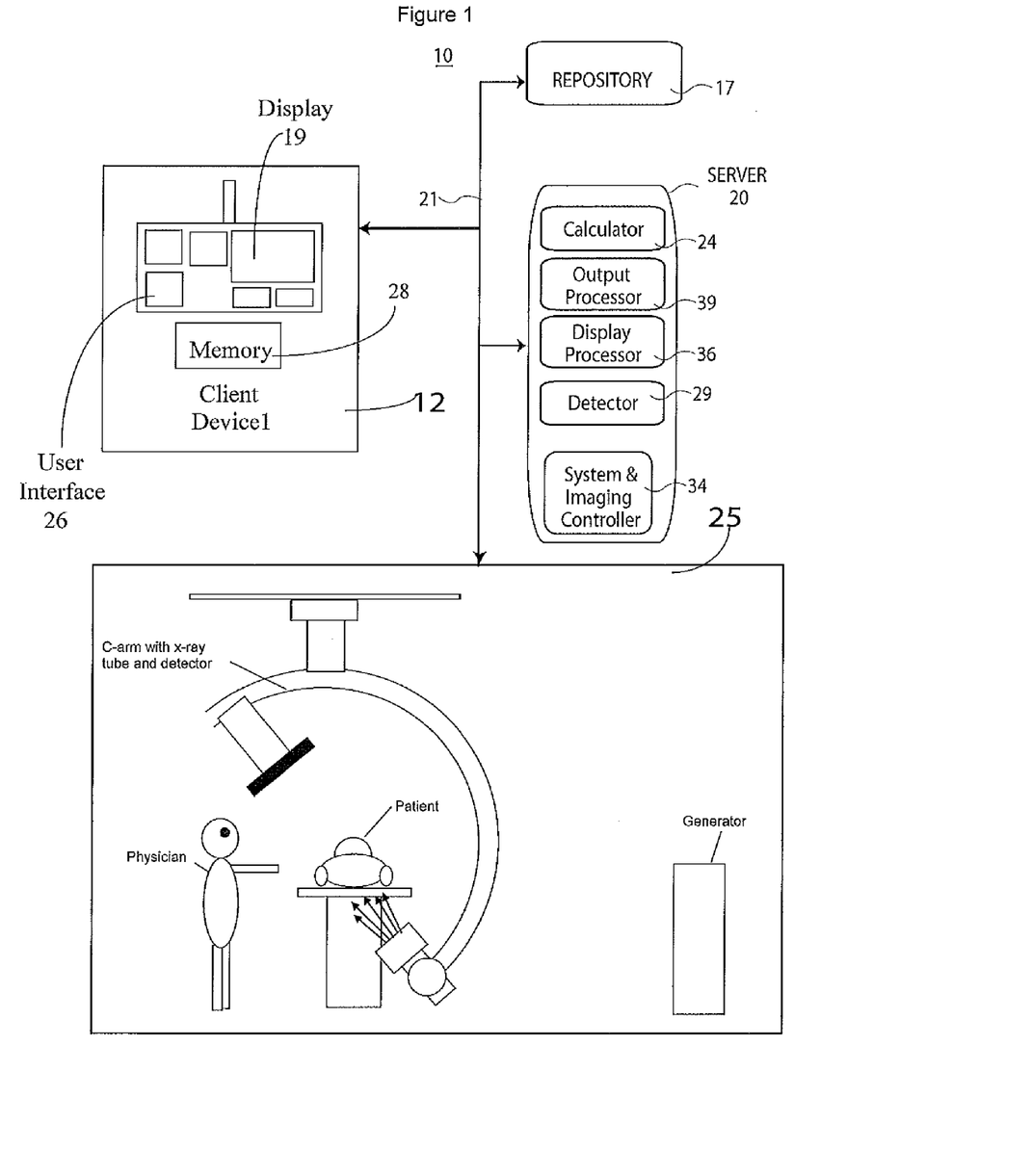
FIG. 1 shows an X-ray imaging system for automatically calculating blood flow travel time, according to invention principles.

FIG. 1 shows an X-ray imaging system 10 for automatically calculating blood flow travel time. System 10 includes one or more processing devices (e.g., workstations or portable devices such as notebooks, Personal Digital Assistants, phones) 12 that individually include a user interface control device 26 such as a keyboard, mouse, touchscreen, voice data entry and interpretation device, display 19 and memory 28. System 10 also includes at least one repository 17, X-ray imaging modality system 25 (which in an alternative embodiment may comprise an MR (magnetic resonance), CT scan, or Ultra-sound system, for example) and server 20 intercommunicating via network 21. X-ray imaging modality system 25 comprises a C-arm that houses an X-ray radiation source device and a detector device mounted at different ends of the C-arm and rotating about a patient table. An associated electrical generator provides electrical power for the X-ray radiation system.

At least one repository 17 stores medical image studies for multiple patients in DICOM compatible (or other) data format. A medical image study individually includes multiple image series of a patient anatomical portion which in turn individually include multiple images. Server 20 includes detector 29, calculator 24, display processor 36, output processor 39 and system and imaging controller 34. Display 19 presents display images comprising a Graphical User Interface (GUI) generated in response to predetermined user (e.g., physician) specific preferences. Imaging controller 34 controls operation of imaging device 25 in response to user commands entered via user interface 26. In alternative arrangements, one or more of the units in server 20 may be located in device 12 or in another device connected to network 21.

X-ray image acquisition system 25 initiates acquisition of images at a second anatomical site synchronized with introduction of contrast agent into a patient vessel at a first anatomical site. Detector 29 automatically compares images, acquired at the second anatomical site in response to the introduction of contrast agent, with images of the second anatomical site acquired in the absence of a contrast agent, to detect when contrast agent reaches the second anatomical site via blood flow in a circulatory system of the patient. Calculator 24 (a calculation processor) automatically calculates a blood flow travel time duration between the first and second anatomical sites based on the time elapsed between time of the introduction of contrast agent and a time the contrast agent reaches the second anatomical site in response to the detection. Output processor 39 automatically generates a message indicating the calculated blood flow travel time. X-ray system controller 34 automatically terminates acquisition of X-ray images in response to the detection of contrast agent reaching the second anatomical site. Display processor 36 generates data representing at least one display image enabling a user to, select a first particular anatomical vessel location as the first anatomical site and select a second particular anatomical vessel location as the second anatomical site.

Figure 2:
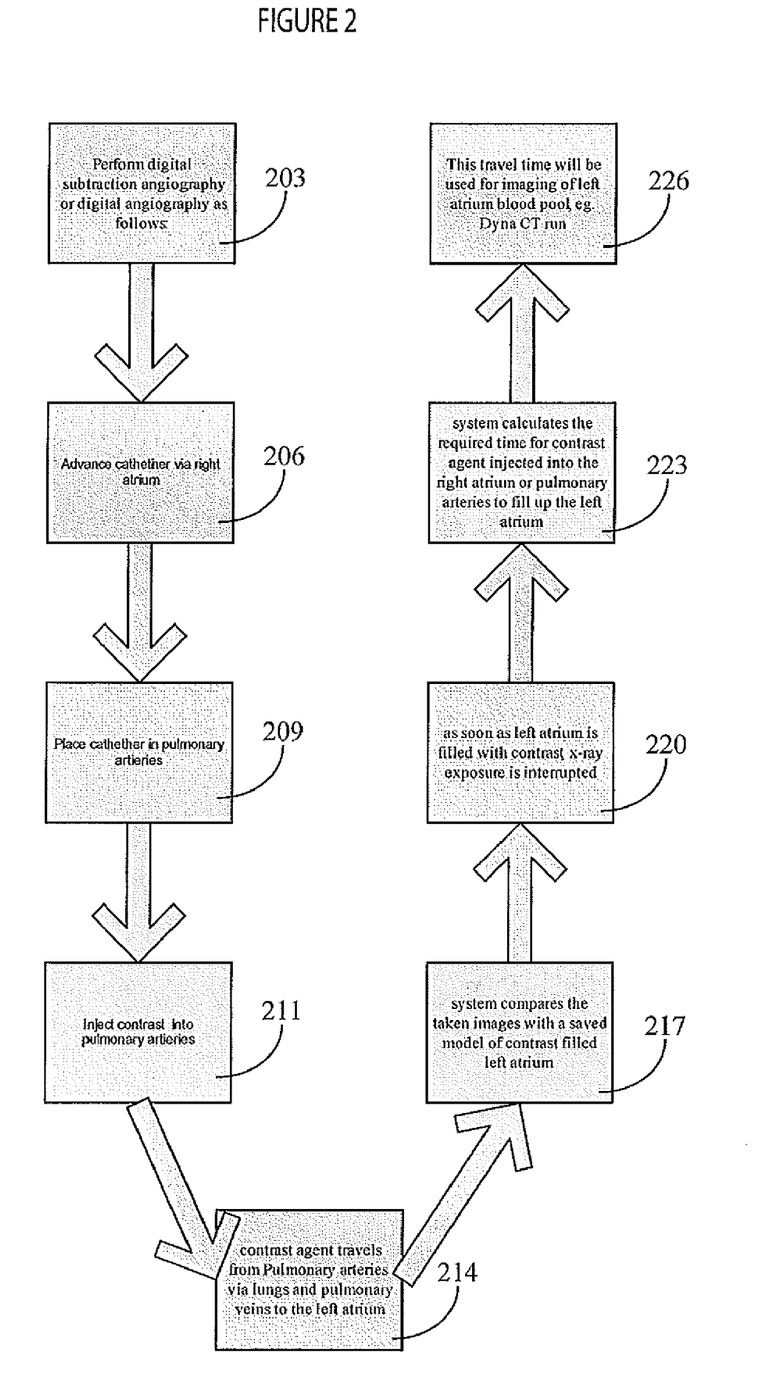
FIG. 2 shows a flowchart of a process for imaging performed by automatically calculating blood flow travel time, according to invention principles.
Figure 3:
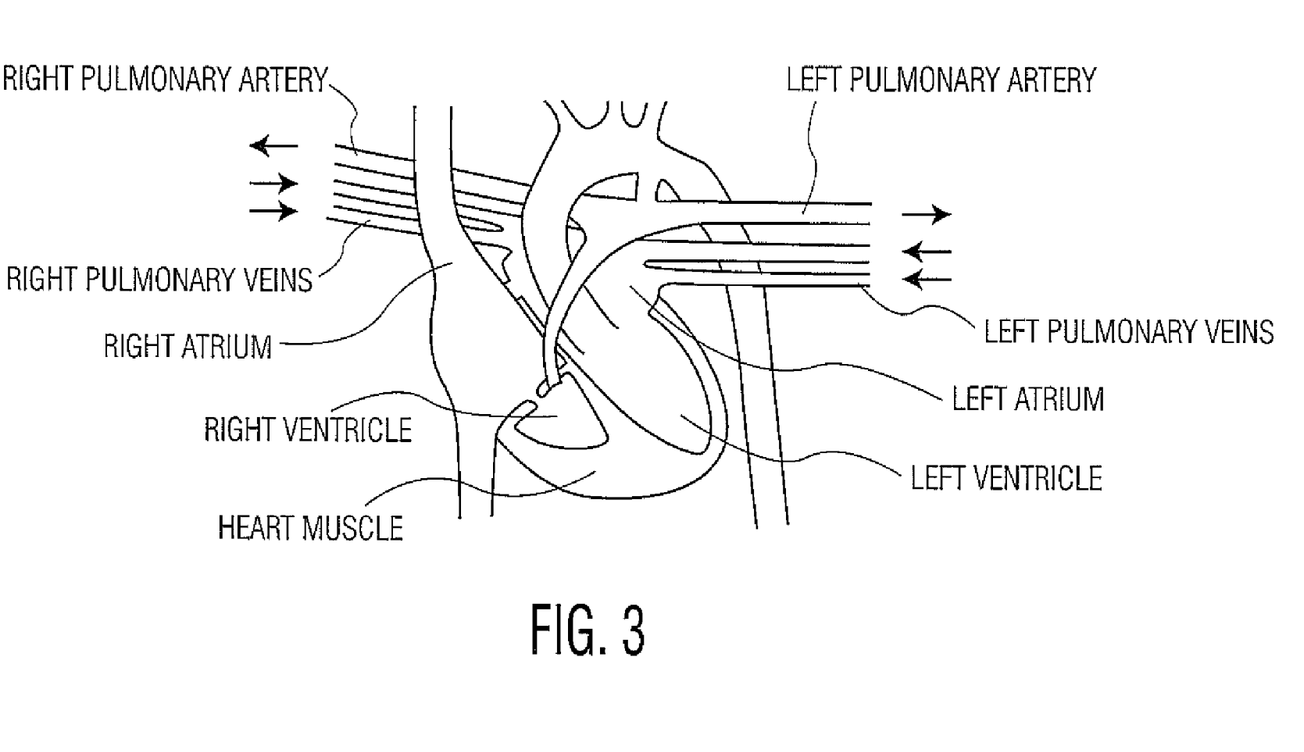
FIG. 3 shows a pulmonary circuit.
Figure 4:
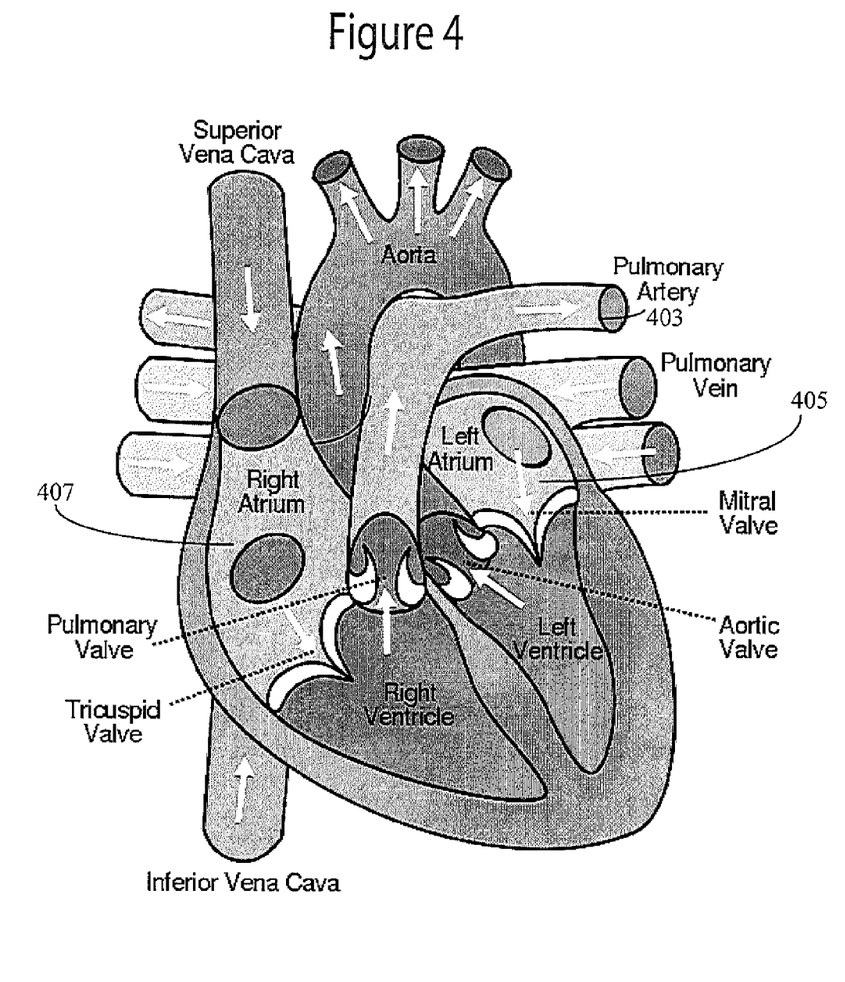
FIG. 4 shows a heart system.

FIG. 2 shows a flowchart of a process for imaging performed by automatically calculating blood flow travel time from a right atrium or pulmonary arteries to the left atrium, for example. FIG. 3 shows a pulmonary circuit indicating pulmonary artery 303, left atrium 305 and right atrium 307. Similarly, FIG. 4 shows a heart system indicating pulmonary artery 403, left atrium 405 and right atrium 407. In step 203, system 10 (FIG. 1) initiates performing digital subtraction angiography or digital angiography on a patient using X-ray imaging system 25. In step 206 a catheter is advanced via a right atrium and in step 209 is placed in pulmonary arteries. Contrast agent is injected into the pulmonary arteries in step 211 and in step 214 the contrast agent travels from the pulmonary arteries via lungs and pulmonary veins to the left atrium. In step 217 detector 29 compares acquired images of the left atrium with previously saved model images of the left atrium of the patient filled with contrast agent. In step 220, in response to detecting the left atrium is filled with contrast agent based on a comparison of acquired and model images, detector 29 interrupts X-ray imaging exposure of the left atrium. In another embodiment X-ray imaging is interrupted by an operator.

Figure 5:
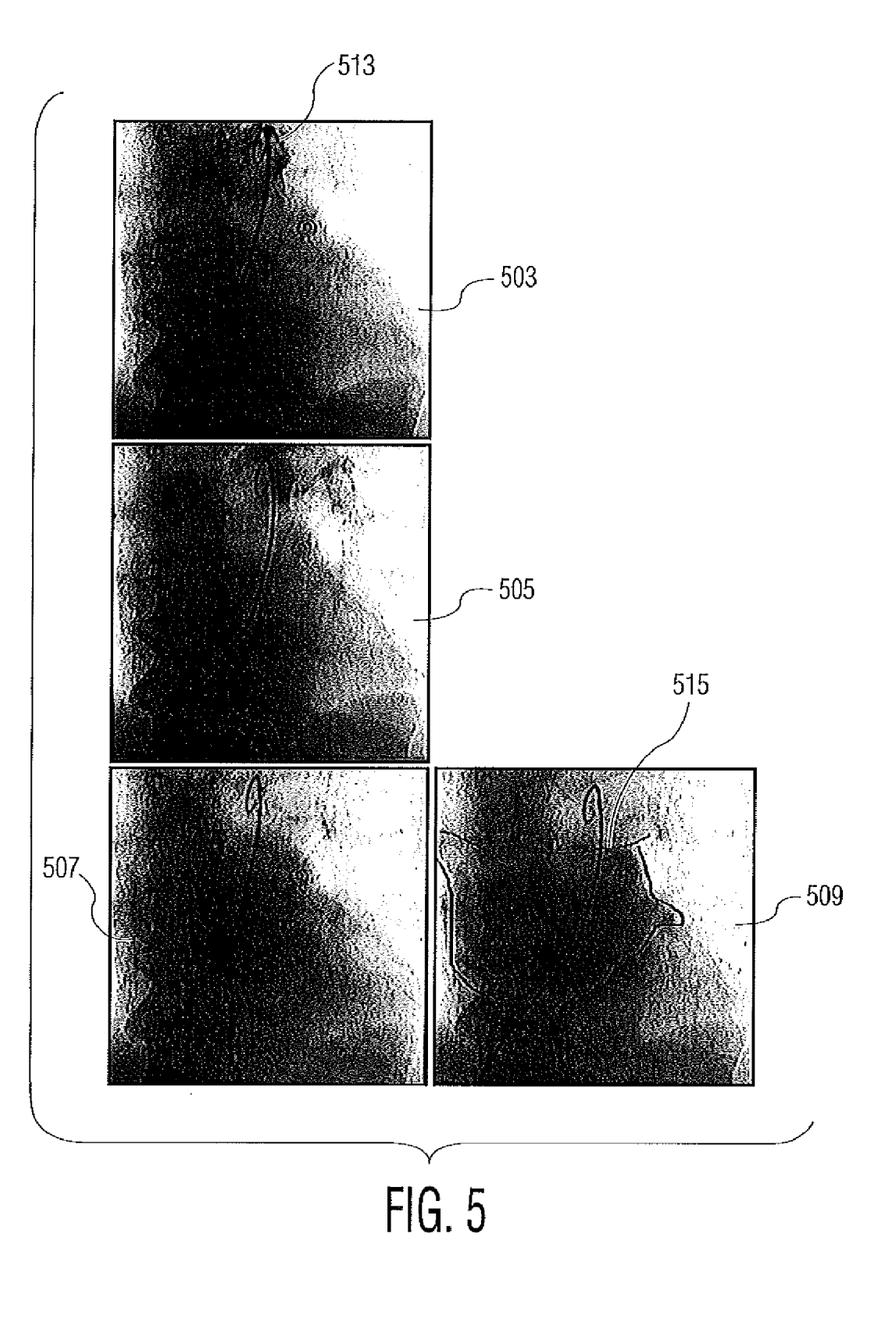
FIG. 5 shows X-ray images illustrating contrast agent flow between anatomical sites, according to invention principles.

Calculator 24 in step 223 calculates the required time for the contrast agent injected into the right atrium or pulmonary arteries to fill up the left atrium as a time difference between initiating introduction of contrast agent in step 211 and time at which detector 29 determines the left atrium is filled up with the agent in step 220. In an example, 15 frames are acquired between start of a contrast agent injection to time of filling of a left atrium and image acquisition is performed at 3 frames per second (3 f/s) so the travel time is 15/3=5 seconds which is the travel time of the contrast agent from pulmonary arteries to the left atrium. FIG. 5 shows X-ray images 503, 505, 507 and 509 illustrating contrast agent flow from pulmonary artery to left atrium. Specifically, contrast agent is injected at a pulmonary artery site 513 in image 503 and starts to fill the left atrium in image area 515 of image 509 via flow in intervening images 505 and 507. In step 226, output processor 39 uses the calculated travel time for imaging a left atrium blood pool. Output processor 39 uses the calculated travel time in rotational angiography for delaying the start of X-ray imaging.

A catheter is placed in the pulmonary artery and the contrast agent is injected there in order to acquire a 3D image of the left atrium. If X-ray imaging is initiated at the time of contrast agent injection, many acquired X-ray images are unusable for 3D imaging of a left atrium. The images that contribute to 3D image of left atrium are the ones that are filled with contrast agent (termed blood pool images). In order to reduce radiation dose exposure of a patient, system 10 uses the calculated travel time to delay X-ray imaging until the contrast agent arrives into the left atrium. The travel time of contrast agent from pulmonary artery to a left atrium differs in patients. The travel time depends on the conditions of the pulmonary arteries, lungs and pulmonary veins. Travel time from pulmonary arteries to a left atrium is usually independent of patient weight and in healthy people is around 5 to 6 seconds, but differs in patients and can be 8 seconds or more, for example. The travel time depends on heart valve conditions, the amount of valve calcification and other factors. System 10 also uses a calculated travel time for controlling timing of performance of a CT scan of a left atrium, for example.

Display processor 36 initiates generation of data representing a UI image enabling a user to select first and second different anatomical points in a circulatory system between which travel time is calculated. In another embodiment a user selects a type of travel time computation from a list of predetermined travel time type calculations. In one implemented embodiment, a 3 frame per second rate was found to be adequate for use in obtaining travel time but higher or lower rates may also be used. The higher rates increase patient radiation exposure however.

Figure 6:
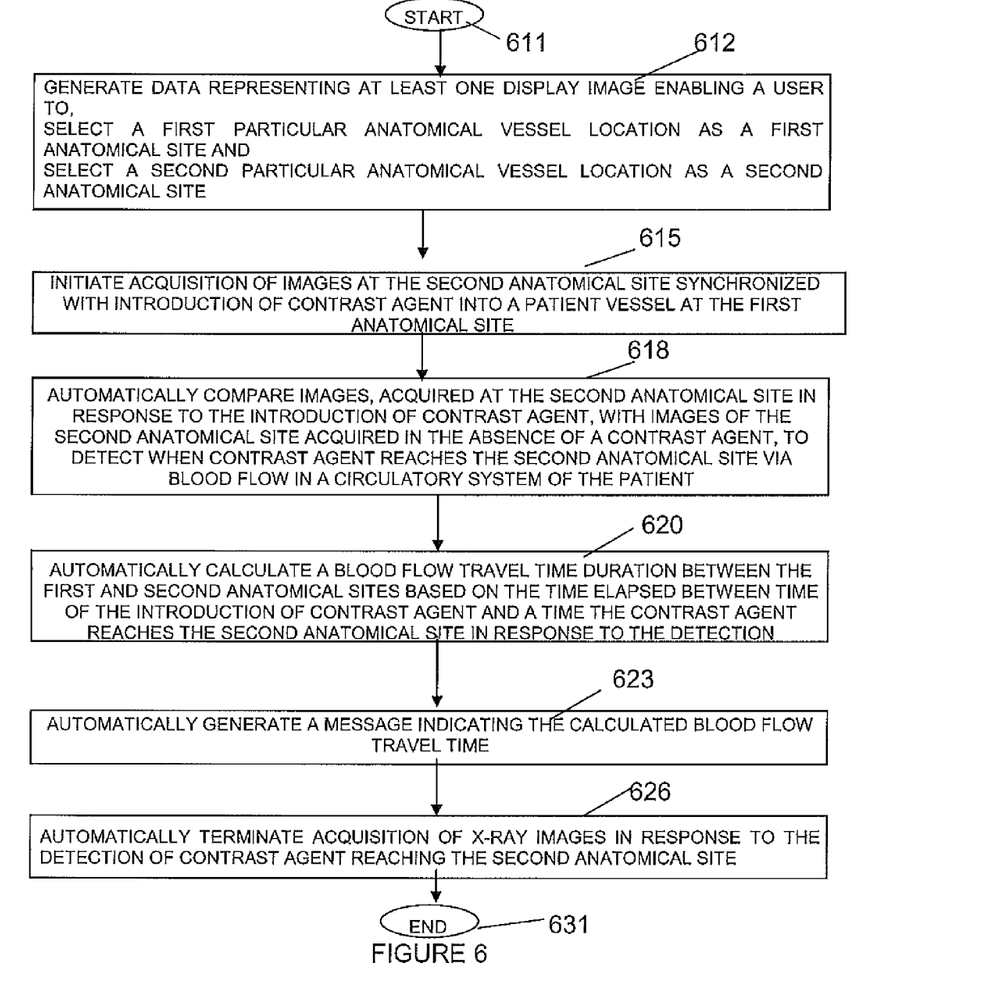
FIG. 6 shows a flowchart of a process used by an X-ray imaging system for automatically calculating blood flow travel time, according to invention principles.

FIG. 6 shows a flowchart of a process used by X-ray imaging system 10 (FIG. 1) for automatically calculating blood flow travel time. In step 612 following the start at step 611, display processor 36 generates data representing at least one display image enabling a user to, select a first particular anatomical vessel location as a first anatomical site and select a second particular anatomical vessel location as a second anatomical site. In step 615, X-ray image acquisition system 25 is used to initiate acquisition of images at the second anatomical site synchronized with introduction of contrast agent into a patient vessel at the first anatomical site.

In step 618 detector 29 automatically compares images, acquired at the second anatomical site in response to the introduction of contrast agent, with images of the second anatomical site acquired in the absence of a contrast agent, to detect when contrast agent reaches the second anatomical site via blood flow in a circulatory system of the patient. Detector 29 also automatically compares images, acquired at the first anatomical site with images of the second anatomical site acquired in the absence of a contrast agent, to detect when contrast agent is introduced into the first anatomical site. Calculator 24 in step 620 automatically calculates (and stores) a blood flow travel time duration between the first and second anatomical sites based on the time elapsed between time of the introduction of contrast agent and a time the contrast agent reaches the second anatomical site in response to the detection. Output processor 39 in step 623 automatically generates a message indicating the calculated blood flow travel time. In one embodiment, output processor 39 automatically generates a message to a user prompting the user to terminate acquisition of X-ray images in response to the detection of contrast agent reaching the second anatomical site. In step 626, X-ray system controller 34 automatically terminates acquisition of X-ray images in response to the detection of contrast agent reaching the second anatomical site.

In one embodiment, the second anatomical site comprises a left atrium heart chamber and the first anatomical site comprises a pulmonary artery. Detector 29 automatically detects when contrast agent reaches the second anatomical site by determining when the heart chamber is filled. Detector 29 further automatically detects when the heart chamber is filled with contrast agent by comparing an image of the heart chamber with previously saved images of the heart chamber of the patient filled with contrast agent. X-ray system controller 34 automatically terminates acquisition of X-ray images in response to the detection the heart chamber of the patient is filled with contrast agent. X-ray image acquisition system 25 also prompts a user via a display image to initiate acquisition of images at the second anatomical site delayed by a time period from the introduction of contrast agent into the patient vessel at the first anatomical site. The delay time period is determined from stored predetermined data indicating minimum blood flow times between the first and second anatomical sites. In addition, display processor 36 generates data representing at least one display image enabling a user to select a type of blood flow travel time determination between particular first and second anatomical sites from multiple different types of blood flow travel time determination. The process of FIG. 6 terminates at step 631.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user.

A user interface (UI), as used herein, comprises one or more display images, generated by a user interface processor and enabling user interaction with a processor or other device and associated data acquisition and processing functions. The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1, 2, 5 and 6 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system advantageously automatically calculates time required for blood to travel from Pulmonary Arteries to the Left Atrium and a calculated time is used for 3D imaging of the left Atrium, for example. Further, the processes and applications may, in alternative embodiments, be located on one or more (e.g., distributed) processing devices on a network linking the units of FIG. 1. Any of the functions and steps provided in FIGS. 1, 2, 5 and 6 may be implemented in hardware, software or a combination of both.

What is claimed is:

1. An X-ray imaging system for automatically calculating blood flow travel time, comprising:
    an X-ray image acquisition system for initiating acquisition of images at a second anatomical site synchronized with introduction of contrast agent into a patient vessel at a first anatomical site;
    a detector for automatically comparing images, acquired at said second anatomical site in response to said introduction of contrast agent, with images of said second anatomical site acquired in the absence of a contrast agent, to detect when contrast agent reaches said second anatomical site via blood flow in a circulatory system of said patient;
    a calculator for automatically calculating a blood flow travel time duration between the first and second anatomical sites based on the time elapsed between time of said introduction of contrast agent and a time said contrast agent reaches said second anatomical site in response to the detection; and
    an output processor for automatically generating a message indicating the calculated blood flow travel time.

2. A system according to claim 1, including
an X-ray system controller for automatically terminating acquisition of X-ray images in response to the detection of contrast agent reaching said second anatomical site.

3. A system according to claim 1, wherein
said output processor automatically generates a message to a user prompting the user to terminate acquisition of X-ray images in response to the detection of contrast agent reaching said second anatomical site.

4. A system according to claim 1, wherein
said second anatomical site comprises a heart chamber and said detector automatically detects when contrast agent reaches said second anatomical site by determining when said heart chamber is filled.

5. A system according to claim 4, wherein
said detector automatically detects when said heart chamber is filled with contrast agent by comparing an image of said heart chamber with previously saved images of the heart chamber of the patient filled with contrast agent.

6. A system according to claim 5, including
an X-ray system controller for automatically terminating acquisition of X-ray images in response to the detection the heart chamber of the patient is filled with contrast agent.

7. A system according to claim 4, wherein
said heart chamber comprises a left atrium and
said first anatomical site comprises a pulmonary artery.

8. A system according to claim 1, including
a display processor for generating data representing at least one display image enabling a user to,
    select a first particular anatomical vessel location as said first anatomical site and
    select a second particular anatomical vessel location as said second anatomical site.

9. A system according to claim 1, including
a display processor for generating data representing at least one display image enabling a user to select a type of blood flow travel time determination between particular first and second anatomical sites from a plurality of different types of blood flow travel time determination.

10. A system according to claim 1, wherein
said X-ray image acquisition system prompts a user via a display image to initiate acquisition of images at said second anatomical site delayed by a time period from said introduction of contrast agent into said patient vessel at said first anatomical site.

11. A system according to claim 10, wherein
said time period being determined from stored predetermined data indicating minimum blood flow times between the first and second anatomical sites.

12. A system according to claim 1, wherein
said detector automatically compares images, acquired at said first anatomical site with images of said second anatomical site acquired in the absence of a contrast agent, to detect when contrast agent is introduced into said first anatomical site.

13. An X-ray imaging system for automatically calculating blood flow travel time, comprising:
 a display processor for generating data representing at least one display image enabling a user to,
  select a first particular anatomical vessel location as a first anatomical site and
  select a second particular anatomical vessel location as a second anatomical site,
 an X-ray image acquisition system for initiating acquisition of images at said second anatomical site synchronized with introduction of contrast agent into a patient vessel at said first anatomical site;
 a detector for automatically comparing images, acquired at said second anatomical site in response to said introduction of contrast agent, with images of said second anatomical site acquired in the absence of a contrast agent, to detect when contrast agent reaches said second anatomical site via blood flow in a circulatory system of said patient;
 a calculator for automatically calculating a blood flow travel time duration between the first and second anatomical sites based on the time elapsed between time of said introduction of contrast agent and a time said contrast agent reaches said second anatomical site in response to the detection; and
 an output processor for automatically generating a message indicating the calculated blood flow travel time.

14. A system according to claim 13, wherein
said second anatomical site comprises a heart chamber and
said detector automatically detects when contrast agent reaches said second anatomical site by determining when said heart chamber is filled.

15. A system according to claim 14, wherein
said detector automatically detects when said heart chamber is filled with contrast agent by comparing an image of said heart chamber with previously saved images of the heart chamber of the patient filled with contrast agent.

16. A system according to claim 15, including
an X-ray system controller for automatically terminating acquisition of X-ray images in response to the detection the heart chamber of the patient is filled with contrast agent.

17. A method for automatically calculating blood flow travel time in an X-ray imaging system, comprising the activities of:
 initiating acquisition of images at a second anatomical site synchronized with introduction of contrast agent into a patient vessel at a first anatomical site;
 automatically comparing images, acquired at said second anatomical site in response to said introduction of contrast agent, with images of said second anatomical site acquired in the absence of a contrast agent, to detect when contrast agent reaches said second anatomical site via blood flow in a circulatory system of said patient;
 automatically calculating a blood flow travel time duration between the first and second anatomical sites based on the time elapsed between time of said introduction of contrast agent and a time said contrast agent reaches said second anatomical site in response to the detection; and
 automatically generating a message indicating the calculated blood flow travel time.

18. A method according to claim 17, wherein
said second anatomical site comprises a heart chamber and
said detector automatically detects when contrast agent reaches said second anatomical site by determining when said heart chamber is filled.

* * * * *